United States Patent
Nurmikko et al.

(10) Patent No.: US 7,064,827 B2
(45) Date of Patent: Jun. 20, 2006

(54) OPTICAL TRACKING AND DETECTION OF PARTICLES BY SOLID STATE ENERGY SOURCES

(75) Inventors: Arto V. Nurmikko, Providence, RI (US); Richard K. Chang, Hamden, CT (US)

(73) Assignee: Brown University Research Foundation, Providence, RI (US)

( * ) Notice: Subject to any disclaimer, the term of this patent is extended or adjusted under 35 U.S.C. 154(b) by 268 days.

(21) Appl. No.: 10/442,795

(22) Filed: May 20, 2003

(65) Prior Publication Data

US 2004/0008345 A1    Jan. 15, 2004

Related U.S. Application Data

(60) Provisional application No. 60/412,198, filed on Sep. 20, 2002, provisional application No. 60/381,763, filed on May 20, 2002.

(51) Int. Cl.
*G01N 21/00* (2006.01)
*G01J 3/30* (2006.01)

(52) U.S. Cl. ............ 356/338; 356/336; 356/317; 356/318

(58) Field of Classification Search ............. 356/317, 356/318, 336, 338, 73; 250/461.2, 461.1, 250/458.1, 459.1
See application file for complete search history.

(56) References Cited

U.S. PATENT DOCUMENTS

| | | | |
|---|---|---|---|
| 4,596,036 A * | 6/1986 | Norgren et al. ............. 382/129 |
| 4,885,473 A * | 12/1989 | Shofner et al. ............. 250/574 |
| 5,133,602 A | 7/1992 | Batchelder et al. ......... 356/375 |
| 5,260,764 A | 11/1993 | Fukuda et al. ................. 355/73 |
| 5,272,354 A * | 12/1993 | Kosaka ........................ 250/574 |
| 5,827,660 A * | 10/1998 | Singer et al. .................. 435/6 |
| 5,854,684 A * | 12/1998 | Stabile et al. ................ 356/440 |
| 5,999,250 A * | 12/1999 | Hairston et al. ............... 356/73 |
| 6,061,132 A | 5/2000 | Girvin et al. ................ 356/336 |
| 6,104,483 A | 8/2000 | Sebok et al. ................. 356/244 |
| 6,111,642 A * | 8/2000 | DeFreez et al. ............. 356/337 |
| 6,184,517 B1 * | 2/2001 | Sawada et al. ........... 250/222.2 |
| 6,233,267 B1 | 5/2001 | Numikko et al. ............. 372/46 |
| 6,256,096 B1 * | 7/2001 | Johnson ....................... 356/335 |
| 6,870,165 B1 * | 3/2005 | Amirkhanian et al. ... 250/458.1 |

* cited by examiner

OTHER PUBLICATIONS

Hecht, Eugene, "Optics", 4th Ed., Pearson Education, Inc. publishing as Addison Wesley, 2002, pp. 603-605 and Figure 13.21.

*Primary Examiner*—Layla G. Lauchman
(74) *Attorney, Agent, or Firm*—Harrington & Smith, LLP

(57) ABSTRACT

A particle detector has a chamber defining a pathway that a target particle follows between an entry and an exit point, a solid-state energy source such as an LED, and a re-emission sensor. The energy source imparts energy to the particle between the two points, and the sensor includes an arcuate or multi-planar lens to focus energy re-emitted by the particle. The particle is identifiable by its re-emitted energy spectrum. A scanner re-directs the beam from a single energy source to track the particle between the entry and exit points. Alternatively, the energy source is a plurality of source elements that each scan the particle at a single position. Another embodiment is a chipscale detector system wherein energy source elements are disposed on a source layer, sensor elements are disposed on a sensor layer, and one or more target particles to be detected are retained on a capture layer disposed therebetween.

21 Claims, 5 Drawing Sheets

OPTICAL TRACKING AND DETECTION OF PARTICLES BY SOLID STATE ENERGY SOURCES

PRIORITY STATEMENT

This application claims priority under 35 U.S.C. § 119(e) to two provisional U.S. Patent Applications: application Ser. No. 60/381,763, filed on May 20, 2002 and entitled "Application of Arrays of Semiconductor Light Emitting Ultraviolet and Visible Sources for Biological Agent Detection"; and application Ser. No. 60/412,198, filed on Sep. 20, 2002 and entitled "A Method for Enhancing Optical Detection of Airborne Particles". The disclosures of the above-referenced provisional applications are hereby incorporated by reference in their entirety.

TECHNICAL FIELD

These teachings relate generally to optical detection of particles by measuring or tracking energy re-emitted from the particle after illumination by a solid-state photoexcitation source such as a semiconductor laser, diode laser, or other UV source. It is particularly directed to imparting energy to the particle over a longer time period than prior art systems to overcome low energy absorption of the particle due to the inherent low power of solid state UV sources.

BACKGROUND

Quick and accurate particle diagnostic capabilities have become increasingly important in identifying and quantifying biological/environmental contaminants and other biological assays, such as anthrax spores in air or reticulocytes in blood. Numerous and varied techniques currently available require precise alignment of independent components, which are typically mounted in a laboratory in a semi-permanent fashion. Portable gas chromatographs/mass spectrometers (GC/MS) remain expensive and often overly complicated for field personnel, who must master numerous and varied equipment. Flow cytometers for blood analysis are more commonplace, but typically employ an expensive argon laser to produce a necessary blue light source, and cannot detect particles in air.

The stimulated Raman effect has been used to identify particular particles or classes thereof. As used herein, the term particle may refer to an individual molecule in addition to its more generic meaning. In general, the spontaneous or stimulated Raman effect begins with a molecule at an initial energy state that then absorbs incident energy, such as monochromatic light in the visible, infrared (IR), or ultraviolet (UV) regions. The energy absorption causes the molecule to temporarily enter an intermediate energy state, and eventually decay back to a resting energy state that differs from the initial energy state. Because of this difference, re-emitted energy (energy emitted on the transition from intermediate to resting states) from the molecule defines a spectral shift over the incident energy. Distribution of this re-emitted energy is known as Raman scattering. Raman spectroscopy, which includes Stokes and anti-Stokes transitions (positive or negative difference between initial and resting energy), may be used to identify the molecule or its characteristics based on the above spectral shift. Rayleigh scattering and Brillouin scattering may be similarly used to detect and identify a particle based on re-emitted energy. When the decay time from intermediate to resting energy state is instantaneous (~$10^{-7}$ seconds), the resulting energy is termed fluorescence. Energy from non-instantaneous decay times is termed phosphorescence.

Detection of airborne biological particles/molecules based on light scattering techniques, as opposed to Raman scattering wherein absorbed energy is re-emitted rather than merely scattered elastically, typically employs a large UV laser whose beam is focused into a single spot within an interrogation chamber into which particles are injected within an air sample. The particle injection takes place through a nozzle that defines a jet stream of carrier gas (e.g. air) within which the particles are flowing along a straight-line trajectory. See, for example, U.S. Pat. No. 5,133,602. Light scattering techniques may be used to detect particles based on size, but appear unable to distinguish between similarly sized particles. Light scattering is particularly useful as a 'trigger' signal to detect when a particle enters a detection or identification chamber. Light scattered from the entering particle may be used to activate an identification sensing system, which uniquely identifies the particle as one of interest or not. That is, the light scattering 'trigger' signal need not distinguish between an anthrax particle and an innocuous dust particle.

Conversely, fluorescence-based optical diagnostic techniques for airborne particles, as well as biologically/chemically specific species identification, provides a potentially efficient method to identify presence or absence of specific biological or particulate targets. Practical limitations on equipment used in Raman and light scattering spectroscopy have limited its application mostly to fixed laboratories. Raman scattering systems may uniquely identify a particle based on natural fluorescence of a bioagent or fluorescence of a protein that uniquely binds to a target bioagent. Some prior art Raman scattering systems employ a helium-neon, argon, or krypton laser, a double-scanning monochromator, a focusing lens system, and photon counting electronics. See, for example, OPTICS, Eugene Hecht, $4^{th}$ Ed., pages 603–605 and FIG. 13.21. The monochromator is required to distinguish between incident energy and re-emitted energy, since unshifted laser light would be scattered along with the Raman spectra. Other prior art systems relied upon a resonant chamber to reflect a laser beam across the target molecule, stimulating more energy transitions that could be measured more reliably. Each of these prior art systems relies upon a high-powered laser to instantaneously (i.e., a single laser pulse or similar time period of target exposure to laser energy) induce fluorescence from the subject particle. Additionally, the related optics appears too sensitive incompatible with the rigors of field detection.

What is needed in the art is a portable optical particle diagnostic system for qualitative identification of target particles and/or molecules of interest, especially biological contaminants.

SUMMARY OF THE PREFERRED EMBODIMENTS

The foregoing and other problems are overcome, and other advantages are realized, in accordance with the presently preferred embodiments of these teachings.

In one aspect of the present invention, a particle detector includes an interrogation chamber, a pump or other means for moving a carrier fluid through the interrogation chamber, a photoexcitation source, and a re-emission sensor for detecting fluorescent or phosphorescent energy. The interrogation chamber defines a pathway between an acquisition point and a privation point along which a particle carried by a carrier fluid may follow. The photoexcitation source defines a first beam and a second beam. In one embodiment, a scanner is disposed between the source and the pathway and re-directs a single beam from a single photoexcitation source along the first and the second beam. In another embodiment, the photoexcitation source is a linear array of source elements, each of which defines a beam directed at one particular point along the pathway. The first beam is directed at the acquisition point at an acquisition time, wherein the acquisition time is the time at which the particle is or is expected to be at the acquisition point. Similarly, the second beam is directed at the privation point at a privation time, which is the time at which the particle is or is expected to be at the acquisition point. The pathway is disposed between the photoexcitation source and the re-emission sensor. The re-emission sensor detects energy that is re-emitted by a particle that may absorb energy from either or both of the first beam and the second beam.

In another aspect of the present invention, a particle detector system is particularly adapted to be scalable to chipscale dimensions. Such a system includes a plurality of photoexcitation elements for emitting UV energy, wherein the photoexcitation elements are disposed along a planar source layer. Also included in the system is a plurality of sensor elements for sensing re-emitted energy, wherein the sensor elements are disposed along a planar sensor layer. Disposed between the source layer and the sensor layer is a capture layer for suspending a target particle between a photoexcitation element and a sensor element. A target particle to be identified may be retained permanently or temporarily by the capture layer, and placed between a photoexcitation element and a sensor element for detection and/or identification.

BRIEF DESCRIPTION OF THE DRAWINGS

The foregoing and other aspects of these teachings are made more evident in the following Detailed Description of the Preferred Embodiments, when read in conjunction with the attached Drawing Figures, wherein.

DETAILED DESCRIPTION OF THE PREFERRED EMBODIMENTS

Figure 1:
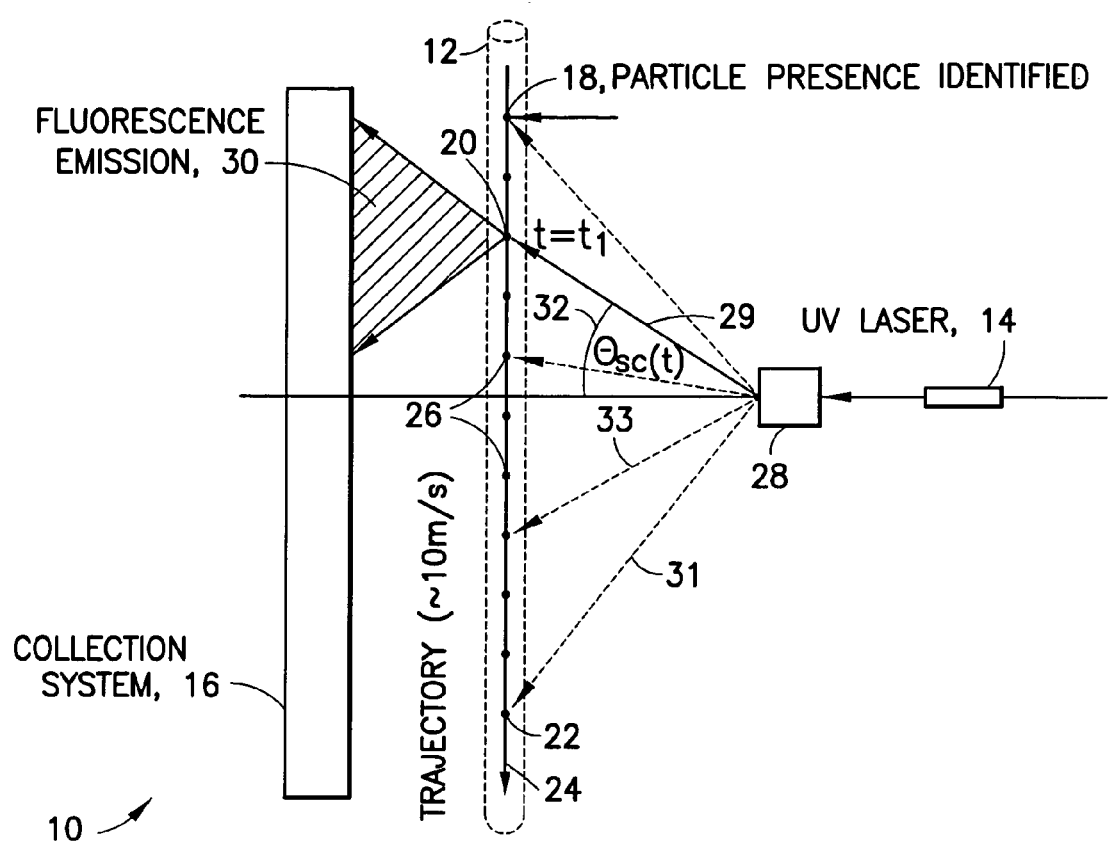
FIG. 1 is a schematic diagram of a particle detector according to a preferred embodiment of the present invention, wherein a UV semiconductor laser scans a moving particle and re-emitted fluorescence is collected for spectral analysis.

Solid-state semiconductor optical sources, such as light emitting diodes (LEDs), diode lasers (DLs), and other UV emitters, are now being developed for the short visible and near ultraviolet spectral range (approximately 350 nm–450 nm) with extension to the ultraviolet (approximately 250 nm–350 nm) subject to ongoing device research. For example, U.S. Pat. No. 6,233,267, entitled "Blue/Ultraviolet/Green Vertical Cavity Surface Emitting Laser Employing Lateral Edge Overgrowth (LEO) Technique", issued on May 15, 2001 and assigned to the same assignee as this application, describes one particular solid state laser in the wavelength range of interest, and is hereby incorporated by reference. Such optical sources offer the advantage of small size (ranging from centimeters to micrometers as currently produced) and low fabrication cost, but are inherently low power. The ultraviolet (UV) range, in particular, can be important in enabling the native fluorescence to be excited of key biological molecular building blocks. Some examples of such building blocks include tryptophan, tyrosine, NADH, riboflavin, and all of the basic amino acids that form the backbone of biological molecules. Target particles to be detected may themselves fluoresce, or may be labeled by fluorescent dyes or tags. Such dyes or tags uniquely bind to a target particle for identification of the target via the unique association. As used herein, energy re-emitted from a target includes energy re-emitted from a biological tag, where a biological tag is used. With the emergence of high efficiency, microscale semiconductor-based UV emitters, these new device technologies can be employed in highly compact fluorescence-based diagnostic systems designed to exploit their advantages, with uses ranging from bioagent warning to biochemically specific assay techniques. Semiconductor lasers/emitters are also useful as sources for studying light scattering from very small particles, and may be used for particle detection via scattering as well as particle identification via fluorescence and/or phosphorescence.

However, solid state UV emitters such as LEDs and DLs deliver much less power than their conventional counterparts, so they cannot merely be substituted into prior art systems or insufficient energy would be absorbed by a target bioagent particle for reliable detection. One aspect of the present invention includes multiple scans of such a particle by one or more photoexcitation sources, such as UV emitters. The present invention uses movement of the particle relative to a beam of photoexcitation energy to impart photoexcitation energy to the particle over a longer period of time, either by multiple pulses or by continuous exposure. Specifically, the present invention exposes a particle to energy on the order of a milliwatt for a total time period on the order of a millisecond. It will be appreciated that in certain embodiments, a determination whether the particle moves relative to the energy beam or the beam moves relative to the particle depends upon a chosen frame of reference. Illustrations and text describe movement of the particle relative to the beam or source. It is stipulated herein that the present invention and claims are not limited to the particular frame of reference selected for the written description.

In accordance with the preferred embodiment of the present invention, FIG. 1 depicts a schematic diagram of a particle detector 10 comprising an interrogation chamber 12, a photoexcitation source 14 such as a solid state laser, a LED, a DL, or other UV emitter, and a sensor 16. Preferably, the photoexcitation source 14 emits a directed beam of UV or blue light. The directed beam may be monochromatic, broadband, or filtered to span a defined spectral width. Preferably, the spectral width of the photoexcitation source 14 does not exceed the spectral width of the desired fluorescence/phosphorescence from the target particle, as described below. The interrogation chamber 12 may be narrow as depicted, or may envelop the sensor 16 and photoexcitation source 14. Depending upon the disposition of the interrogation chamber 12, it may be transparent to energy defined by wavelengths detailed herein. Operation of the particle detector 10 defines an acquisition point 20, a privation point 22, and a pathway 24 therebetween that lies within the interrogation chamber 12. The particle 18 is suspended in a carrier fluid (not shown) such as air, an inert gas, a liquid, or other such transport mechanism that transports the particle along the pathway 24 within the interrogation chamber 12. Due to Brownian or other motion of a particle that may cause it to vary from movement along a line of predominant movement of the carrier fluid, the pathway 24 may not necessarily be a straight line. The carrier fluid is moved through the interrogation chamber 12 by a pump (not shown) or other differential pressure means known in the art, or carried along a moveable solid substrate.

The acquisition point 20 is that point at which the particle 18, on a single pass through the interrogation chamber 12, first re-emits energy that is sensed by the sensor 16. The privation point 22 is that point at which the particle 18, on a single pass through the interrogation chamber 12, last re-emits energy that is sensed by the sensor 16. Re-emitted energy is herein stipulated as energy emanating from the particle 18 in response to the application of photoexcitation energy to the particle 18, and resulting from transition from one energy state to another energy state. Re-emitted energy is thereby distinguished from incident energy that is scattered from the particle 18 without altering an energy state of the particle 18. In addition to fluorescent energy from spectral emission, re-emitted energy also includes an absence of energy due to spectral absorption. In phosphorescence, absorbed energy may be emitted after the particle exits the interrogation chamber 12, but immediately upon absorbing incident energy, there is a gap in spectral bandwidth of energy scattered from the particle. Such a gap represents energy absorbed by the particle 18. A particle identifiable by phosphorescence exhibiting with a long decay time may be instantaneously detected by means of the absorption band, just as fluorescence may be instantaneously detected by the emission band. In other words, measuring the absence of energy in an absorption band is equivalent to measuring the presence of energy in an emission band for purposes of this description and claims.

Disposed between the photoexcitation source 14 and the pathway 24 is a scanner 28 or other means for redirecting the beam of energy from the photoexcitation source 14. The scanner may be a beam deflector based on acousto-optics, microelectromechanical systems (MEMS), or electro-optics. The scanner 28 re-directs the beam emanating from the source 14 to various points along the pathway 24 when the particle 18 is anticipated to be crossing that particular point. For example, once the particle 18 is detected to be within the interrogation chamber 12, the scanner 28 re-directs the energy beam from the source 14 along a first beam 29 to the acquisition point at an acquisition time $t=t_1$ for example, as depicted in FIG. 1. At the acquisition time $t_1$, the particle re-emits energy in a re-emission cone 30 that is qualitatively and quantitatively sensed by the sensor 16. In the preferred embodiment, the sensor 16 is a micro-optical fluorescence collection system arranged in a cylinder and disposed such that the cylindrical axis substantially parallels the pathway 12. The particle 18 may be detected, such as by a light scattering system described above, at a point that may or may not be coincident with the acquisition point 20. At a privation time $t=t_2$ that is later than $t_1$, the particle 18 passes through the privation point 22 and the scanner 28 re-directs the beam of energy from the photoexcitation source 14 along a second beam 31 to the privation point 22. The particle absorbs and re-emits energy as noted above with regard to time $t_1$, and the re-emitted energy is also sensed at the sensor 16.

The particle 18 passes through a series of intermediate points 26 at a series of intermediate times $t_1 < t_{intermediate} < t_2$ between the acquisition point 20 and the privation point 22. Preferably, the scanner 28 re-directs the beam from the photoexcitation source 14 as a series of intermediate beams 33 to the particle 18 continuously at all times between the times $t_1$ and $t_2$. Alternatively, such as with a pulsed laser, the scanner 28 re-directs the beam from the photoexcitation source 14, as intermediate beams 33 that do not vary continuously over time, to the particle 18 at a non-continuous plurality of interim times between the times $t_1$ and $t_2$. Ideally the interval between intermediate times substantially equals the interval between laser pulses. Depending upon focal spot size at the pathway 24, even a pulsed laser may continuously impart energy to the particle 18. Regardless, the scanner 28 causes the beam of energy from the photoexcitation source 14 to be re-directed so as to 'follow' or track the particle 18 as it passes through the interrogation chamber 12.

Specifically, the particle velocity is known (within certain limits imposed by random motion) from the measurable velocity of the carrier fluid or speed/pressure differential of the associated pump. Once a trigger signal indicates the presence of a particle 18 in the jetstream, electronics to enable the scanner 28 to cause the beam to properly track the particle 18 may be activated. The angular rate of the scanner 28 can be controlled based on the calculated particle velocity in such a manner that the particle 18 is continuously illuminated by the continuous wave (or illuminated substantially continuously by a pulsed wave) UV laser source 14 throughout its flight path within the interrogation chamber 12, for the purpose of efficient fluorescence excitation.

The laser beam from the photoexcitation source 14 may be focused to approximately the size of the particle 18. In this manner, the brightness of the UV laser can be utilized effectively during the full transit of the particle 18 within the interrogation chamber 12, as the UV 'spotlight' scans the pre-calculated trajectory. As a consequence, a very large enhancement is achieved in the delivery of photons and the total amount of photoexcitation delivered to the particle 18, in comparison with the conventional schemes whereby a spatially fixed (i.e. non-scanned) laser beam is utilized. In this manner, for example, the energy re-emitted by the particle 18 produces a line image along the sensor 16. In the arrangement of FIG. 1, the line image is vertical. The sensor 16 is particularly adapted to collect data along the line, such as by employing a single cylindrical lens or an array of microlenses distributed along the line, with surface contours that create the cylindrical lens effect. The cylindrical lens or line of micro lenses focuses the re-emitted energy from each discrete or continuously varying re-emission cones 30 onto underlying photo-sensing elements of the sensor 16. Such an arrangement maximizes energy intensity at the photo-sensing elements to offset the low power of the solid state UV source 14 and the resultant low level of absorption and re-emission by the particle 18. Alternatively, the cylindrical lens may be any arcuate or multi-planar shape that concentrates energy from the emission cone 30 onto an element or line of elements of the sensor 16.

One particular embodiment of the scanner 28 comprises an acousto-optic (AO) modulator/deflector disposed as in FIG. 1. Scanning of the beam from the photoexcitation source 14 is accomplished by sweeping the frequency of the electronic signal generator that actuates the piezoelectric transducer in the AO-element, launching an ultrasound wave that diffracts the UV laser beam. Assuming a typical particle velocity of 10 m/sec, a particle interrogation length of 1 cm, a UV laser focal spot size at the location of the particle of 100 micrometers, and a distance of about 5 cm from the acousto-optic crystal (output of scanner 28) to the pathway 24 followed by the particle 18, the beam must scan an angle of approximately 10 degrees in 1 millisecond.

Alternative embodiments of the scanner 28, which can be synchronized to the flow of a particle 18 along the pathway 24, include MEMS-mirrors, as well as electro-optic beam deflectors, though the electrical and electronic requirements may differ from those applicable to the AO-modulator scanner 28 detailed above.

The above description entails determining a position of the particle 18 along the pathway 24 based only on carrier fluid characteristics and one (initial) measured position of the particle 18. More positive determination of the position of the particle 18 along the pathway 24 includes active and preferably real time feedback from the sensor 16 to the scanner 28. As mentioned above, even at a high carrier fluid velocity, there is an appreciable component to the particle's velocity that does not lie along a straight line from the acquisition point 20 to the privation point 22. This lateral uncertainty suggests that the illuminating spot size by the UV laser/emitter source 14 be manipulated to be generally significantly larger than the size of the particle 18. However, such an approach would result in some of the energy of the beam from the scanner 28 missing the particle 18 and increasing opto-electrical noise at the sensor 16.

Figure 2:
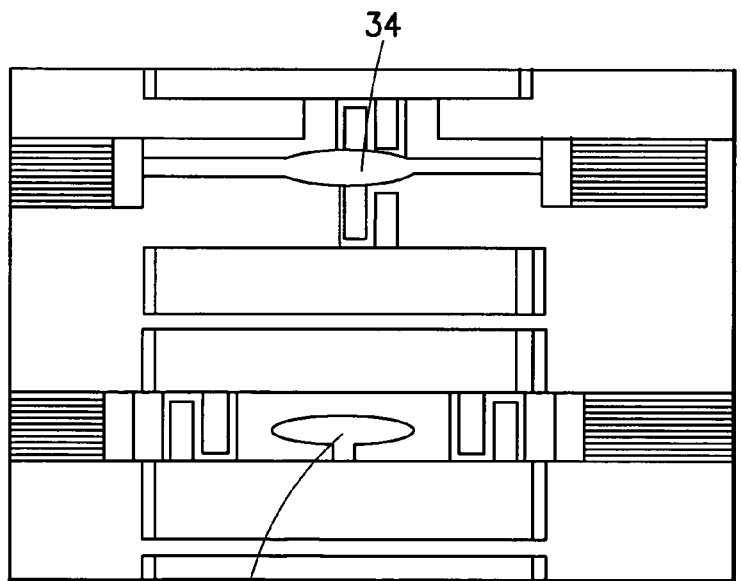
FIG. 2 is a microphotograph of two prior art arcuate mirror elements in a two-dimensional MEMS array that may be used in the present invention.

One suitable technology with applications for active feedback embodiments of the present invention is loosely termed "smart mirrors" or "smart deflectors". Such components segment a curved optical surface to multiple elements, which are individually electromechanically controlled. In so doing, the reflecting and focusing characteristics of the mirror can be fully controlled, both in terms of the directionality of the reflected/deflected laser beam as well as its location and focal spot size. As an illustration of the MEMS technology, FIG. 2 shows a prior art device based on established fabrication techniques for silicon (in this case, laser on sapphire). Two of the circular mirror elements of a large array are indicated and labeled 34 and 36. For use in the present invention, such circular mirror elements 34, 36 may be equipped with individual micro lenses for beam focusing to provide a focal spot size on the order of the particle size. Each mirror element 34, 36 is independently controlled, so the mirror elements 34, 36 provide for a responsive scanner that facilitates bioparticle detection.

Figure 3:
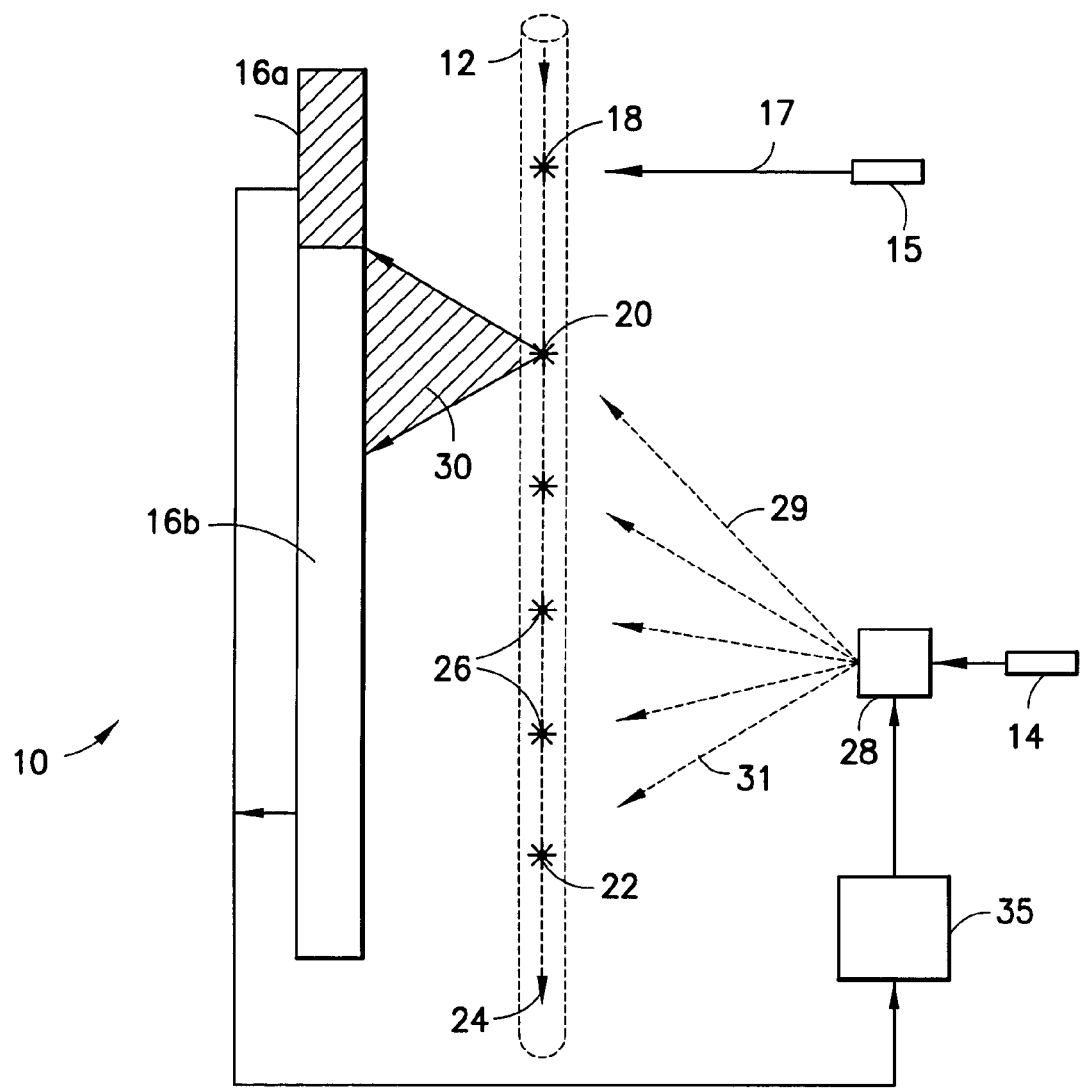
FIG. 3 is a schematic diagram showing a detector beam source separate from a photoexcitation source, according to an embodiment of the invention.

Two embodiments of active feedback scanners are presented. In a first embodiment, information about the particle 18 location along the pathway 24 is acquired by the same semiconductor energy source 14 that provides the fluorescent excitation to the particle 18. Specifically, the scanner is electrically coupled to the sensor to maintain tracking at a point along the pathway that maximized re-emitted energy sensed by the particle. This first embodiment has the advantage that it uses the same photoexcitation source 14 and sensor 16 as the particle detector 10 previously described, and need only add electronic manipulation of optically sensed signals to control the scanner 28. In a second embodiment shown schematically in FIG. 3, a separate energy source 15, preferably defining a longer wavelength (e.g. red), emits a detector beam 17 to scatter energy from the particle 18. A series of photodetectors sensitive to the wavelength of the scattered energy are positioned at a first section 16a of the sensor 16. Photodetectors sensitive to re-emitted wavelength energy due to fluorescence are disposed along a second section 16b of the sensor 16. The photoexcitation source 14 that induces re-emitted energy is controlled by electronics that seek to maximize scattered energy sensed by the photodetectors. In the embodiment of FIG. 3, an input from photodetectors at the first section 16a of the sensor is used in an active feedback loop 35 to power on the photoexcitation source 14 and initiate the scanner 28 to direct the first beam 29 at the acquisition point 20 at the acquisition time $t_1$. The re-emission cone 30 from the particle at the acquisition point 20 is sensed by photodetectors at the second section 16b, which provide an input to the feedback loop 35 for actuating the scanner 28 to direct a beam at the particle 18 at the next subsequent position along the pathway 24, whether the particle 18 is scanned continuously or discretely. The photodetectors in the second section 16b provide real time particle 18 positional information to the scanner 28 so that the energy beam is precisely directed. The feedback loop 35 of either embodiment provides an adjustable feedback so that the fluorescence/scattered light is maintained at a maximum level as the energy beam from the photoexcitation source 14 tracks the bioparticle 18 along the pathway 24 within the optical interrogation chamber 12.

Figure 4:
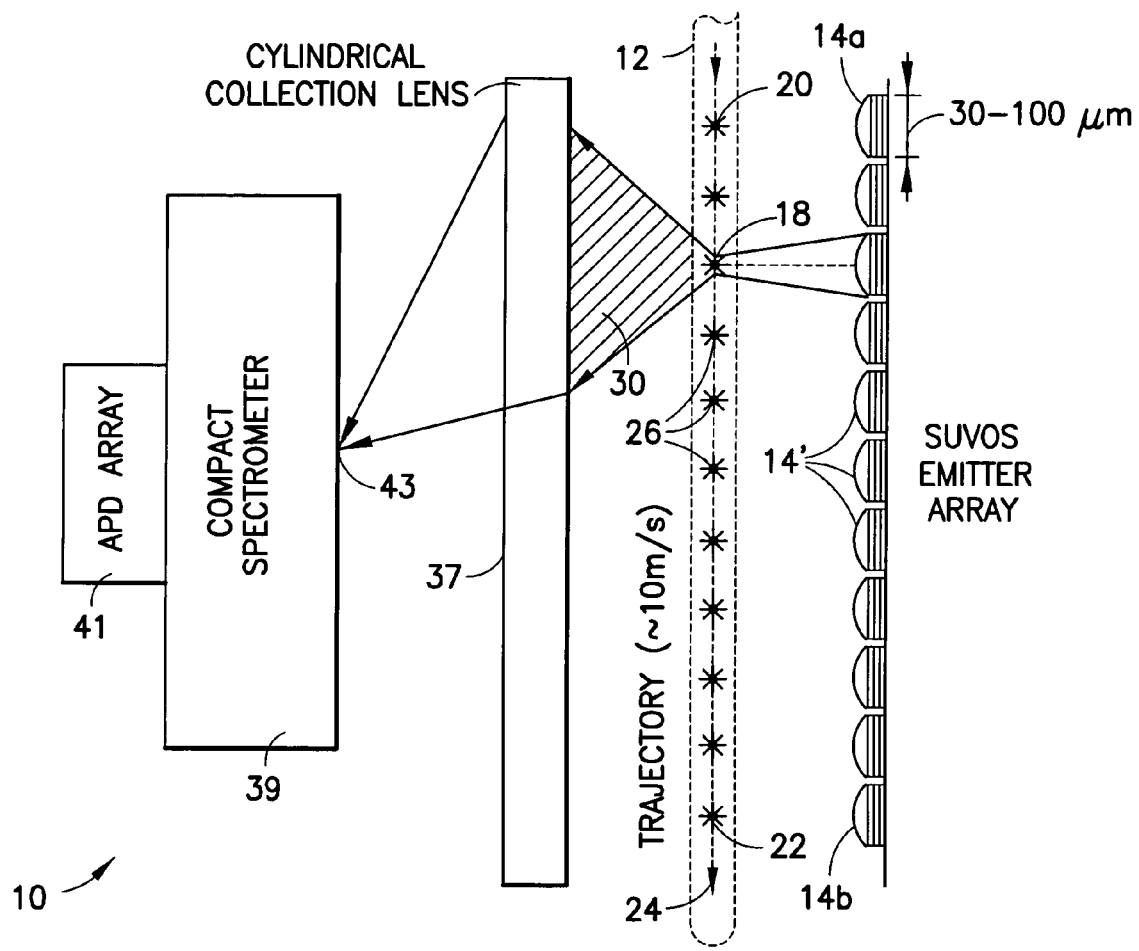
FIG. 4 is a schematic diagram of a linear array of semiconductor ultraviolet optical sources (SUVOS) wherein each source is equipped with a micro lens and illuminates a moving particle at a particular instant.

An alternative embodiment of a particle detector according to the present invention is depicted in the schematic diagram of FIG. 4, wherein the particle detector 10 comprises a plurality of photoexcitation sources 14 and need not include the scanner 28 of FIG. 1. Specifically, the alternative embodiment of FIG. 4 includes a plurality of photoexcitation sources 14 arranged in a line that substantially parallels the pathway 14. Each photoexcitation source imparts energy to a particle traveling along the pathway 24 only once while the particle 18 passes through the interrogation chamber 12, preferably along a line perpendicular to the pathway 24 rather than at a time-dependent angle $\theta_{sc(t)}$ depicted at FIG. 1. When formed as an array as described below, each photoexcitation source 14a, 14', 14b may be switched on and off at very high speeds (on the order of nanoseconds). A first photoexcitation source 14a imparts energy to the particle 18 when the particle 18 is at the acquisition point 20 at the acquisition time $t_1$, and a second photoexcitation source 14b imparts energy to the particle 18 when the particle 18 is located at the privation point 22 at the privation time $t_2$. Preferably, a plurality of interim photoexcitation sources 14' are disposed between the first 14a and last 14b source and impart energy to the particle 18 when the particle 18 is between the acquisition point 20 and the privation point 22 at intermediate times $t_1 < t_{intermediate} < t_2$. Where a particle 18 is carried by a carrier fluid of known velocity through the interrogation chamber 12, power maybe applied to the individual photoexcitation sources 14a, 14', 14b, sequentially based on either the measured initial position of the particle at detection and the carrier fluid velocity. Alternatively, active feedback may be used as detailed above to accurately sequence the application of power to the individual photoexcitation sources 14a, 14', 14b, in the array. A particle 18 may be continuously illuminated using the array of photoexcitation sources 14a, 14', 14b, by increasing their focal spot size so that beam separation at the pathway 24 is less than a particle diameter. Preferably, the array of sources 14a, 14', 14b impart energy to the particle 18 in a less than continuous manner, but substantially continuous due to proximity of the sources 14a, 14', 14b to one another.

The photon sensing system of FIG. 4 differs from that previously described. Energy from the re-emission cone 30 is focused by a cylindrical collection lens 37 onto a collection point 43 that is a gateway to a spectrometer 39 and an avalanche photodiode array (APD) 41 or other quantitative analyzer. The cylindrical collection lens 37 may be cylindrical, hemi-spherical, arcuate, multi-planar, or other such geometry having a convex portion adjacent to the pathway 24 as in FIGS. 1 and 3. The cylindrical lens 37 may be adapted to focus only selected portions of the re-emission cone 30 associated with each of the points 20, 22, 26 along the pathway 24 onto the focal point 43. The collection point 43 is a photonic gateway to a compact spectrometer 39, and may be a slit, a grating, a prism, or some other optical device. The combination spectrometer 39 and APD array 41 are responsive to the wavelengths of interest.

Figure 5:
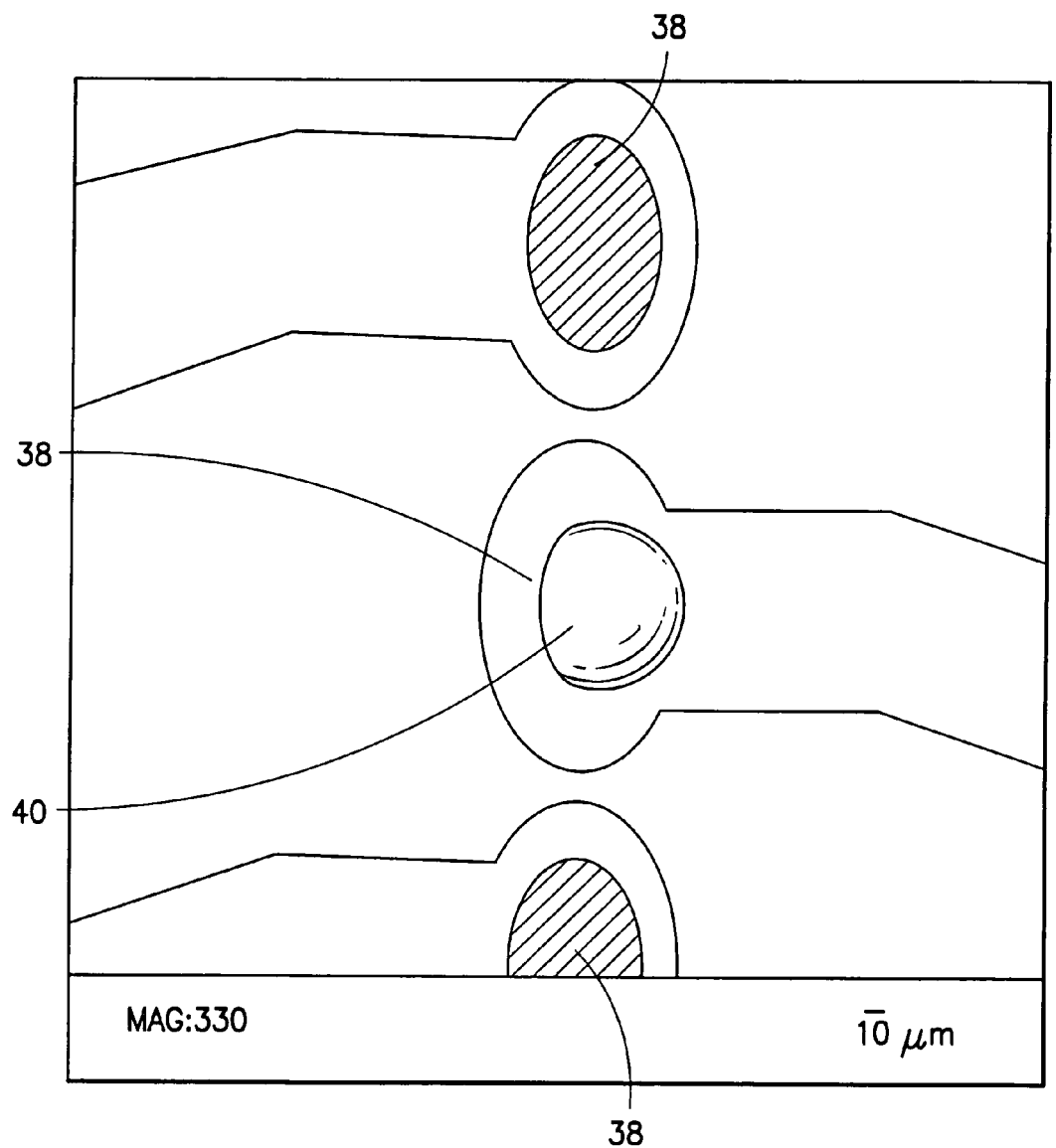
FIG. 5 is a micrograph showing three elements of a 100 element linear array of 340 nm UV LEDs fabricated at Brown University, wherein the central element includes a micro lens for illustration.

FIG. 5 is a micrograph showing three elements of a 100 element linear array of UV LEDs, each measuring approximately 340 nm in diameter. For illustration, the central LED 38 is capped with a micro lens 40 to demonstrate the optical diversity that can be achieved. The array of photoexcitation sources 14a, 14b, 14' are preferably from the gallium nitride family of semiconductors, including combinations of gallium, aluminum, indium, and/or nitrogen, in a thin crystalline multilayer. The compositional and structural details of the layers determine the wavelength of emission of LEDs and LDs. The actual light emitting layers, specifically the quantum well described in U.S. Pat. No. 6,233,267 and incorporated above, can be designed and synthesized for emission in a wide range, from approximately 250 to approximately 500 nm. Two sets of different quantum wells can be embedded within a single photoexcitation source 14a, 14b, 14', wherein electrically separate contacts to each quantum well segment is facilitated by a tunnel junction spacer. This enables a dual-wavelength emission to take place in a single LED, and is applicable for a single energy source 14 as in FIG. 1 or in an array of photoexcitation sources 14a, 14', 14b as in FIG. 4. Because the underlying light-emitting material of the photoexcitation source 14a, 14', 14b, can be synthesized to include several different quantum wells, the fabrication of the array with UV sources that transmit in multiple wavelengths enriches the spectroscopic specificity of the fluorescence excitation scheme.

Semiconductor-based LEDs and LDs are inherently low power devices, generally on the order of one milliwatt. Each device measures on the order of 1 millimeter square. They can be fabricated as multi-element arrays due to their planar underlying material structure. The photoexcitation of a particle 18 moving relative to a source 14 provides a fluorescent "line" image for subsequent collection and spectral analysis at the sensor 16, thereby greatly reducing the high peak power demands for individual LEDs/LDs that would otherwise be required for sufficient particle energy absorption from a single, short-term beam. The underlying light emitting material of the photoexcitation source 14 can be synthesized to include several different quantum wells to enrich the spectroscopic specificity of the fluorescence excitation scheme. Specifically, more than one wavelength emanating from the photoexcitation source 14 can scan for different fluorescent or phosphorescent 'signatures' from various particles 18, as sensed at the sensor 16.

Increasing focal spot size imposes certain disadvantages detailed above. An alternative approach to compensate for uncertainty as to the particle's position in the plane perpendicular to the pathway 24 is to deploy more than one array of linearly disposed photoexcitation sources 14a, 14', 14b, each linear array along a line substantially parallel to the pathway 24. Such an arrangement increases the spatial coverage of the photoexcitation in the described plane, significantly enhancing optical efficiency.

Figure 6:
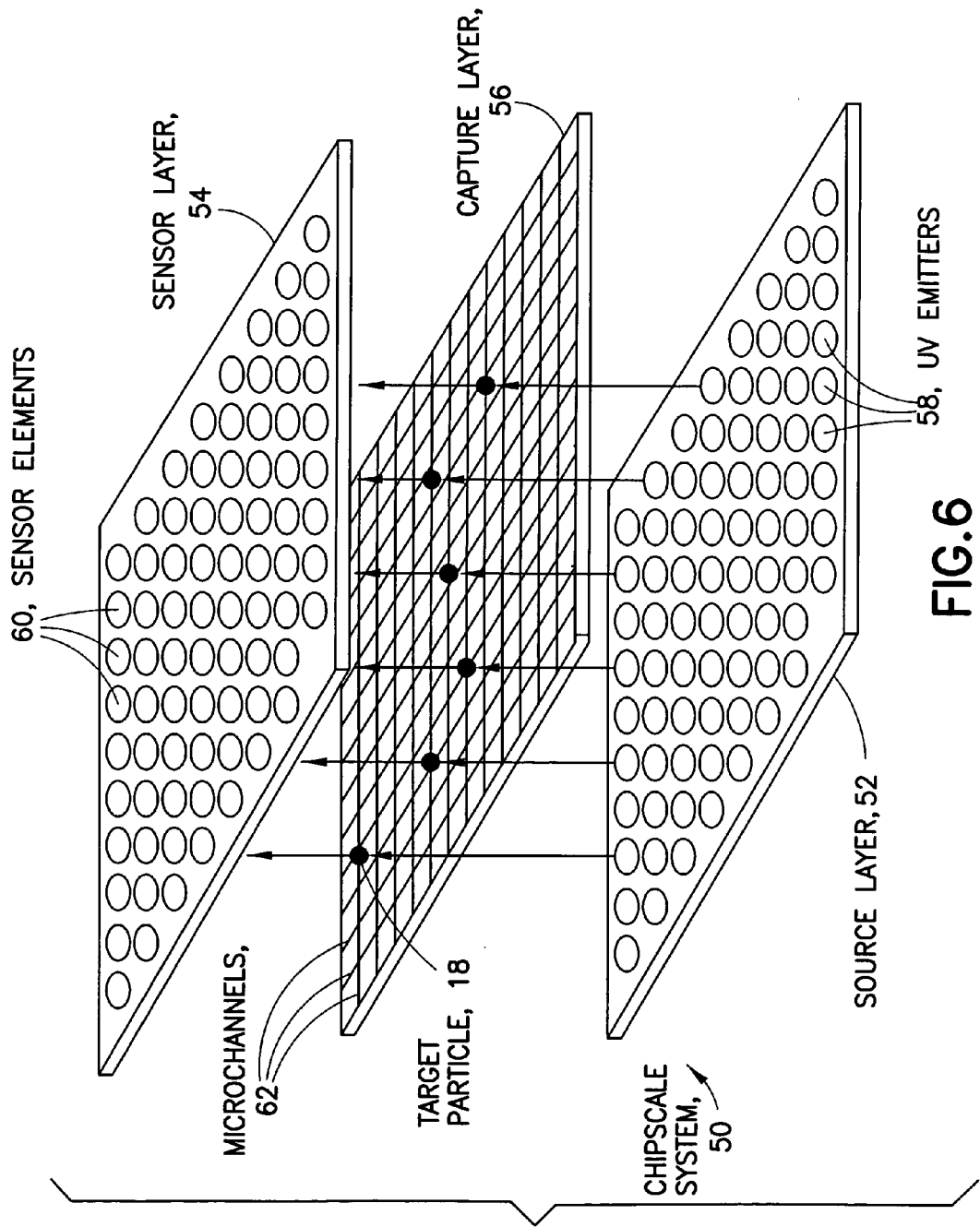
FIG. 6 is a schematic diagram of a planar chipscale particle detection system.

State-of-the art planar micro-optical and microfluidic components can enable miniaturization of a complete optical particle detector system to the chipscale, shown schematically in FIG. 6. Generally, such a chipscale system 50 includes a photoexcitation source layer 52, a sensor layer 54, and a specimen capture layer 56 disposed therebetween. It will be appreciated that each of the afore-mentioned layers 52, 54, 56 are fabricated from a plurality of sub-layers (not shown). Preferably, the source layer 52 defines a plurality of individual photoexcitation source elements 58 such as a semiconductor LED, LD, or other solid state UV emitter. The sensor layer 54 defines a plurality of sensor elements 60 for sensing energy re-emitted by particles 18 that may be captured on a surface or enveloped within microchannels 62 of the capture layer 56. The layers 52, 54, 56 are assembled into a monolithic unit such that the sensor elements 60 are aligned with corresponding source elements 58.

In the chipscale system 50, the bioagent particles may be attached to a solid surface by either physical means (electrostatic capture) or by molecular bonding to classes of proteins (antibodies) pre-disposed between a source element 58 and a sensor element 60. While the principal benefit of anchoring the bioagent particles is a greatly improved fluorescence yield (particles are quasi-stationary) in conjunction with 2-dimensional emitter arrays, as well as compacting the system 50 increasingly to the chipscale, the choice of antibodies can further narrow the classes of biological substances. Ideally, a chipscale particle detector system 50 uses antibodies that are bacteria/spore specific so that fluorescent labeling of molecular sites at the spore/antibody interface (receptors) enables at least partial species identification. Such antibody techniques (with robust proteins) do not require an on-chip (biochemical) wet lab; only simple buffered solutions are required (as opposed to those as encountered with usual microbiological assay approaches). Various antibodies may be disposed on the capture layer 56 to bind any of several types of target particles 18, or a single type of antibody may be disposed for more statistically reliable identification of the target particle.

In summary then, the present invention as described herein provides a cost effective and efficient device for field identification of target particles such as bioagents, environmental contaminants, or any other particle/molecule that can be made to fluoresce or phosphoresce (either naturally or by selective binding with a particle that itself fluoresces or phosphoresces). Target particles 18 may be bound to a substrate in a chipscale particle detection system 50, or may be suspended in a carrier fluid such as air in other embodiments.

While described in the context of presently preferred embodiments, those skilled in the art should appreciate that various modifications of and alterations to the foregoing embodiments can be made, and that all such modifications and alterations remain within the scope of this invention. Examples herein are stipulated as illustrative and not exhaustive.

What is claimed is:

1. A particle detector comprising:
   an interrogation chamber defining a pathway between an acquisition point and a privation point;
   means for moving a carrier fluid through the pathway;
   a plurality of photoexcitation elements arranged such that a first beam from a first photoexcitation element is directed at the acquisition point at an acquisition time and a second beam from a second photoexcitation element is directed at the privation point at a privation time; and a re-emission sensor for detecting energy of a defined spectrum that is re-emitted by a particle that absorbs energy from at least one of the first beam and the second beam.

2. The detector of claim 1 wherein the re-emission sensor comprises a lens defining at least one arcuate surface adjacent to the pathway and at least one focal point opposite the arcuate surface.

3. The detector of claim 2 wherein the at least two focal points define a line that is substantially parallel to a line defined by the acquisition point and the privation point.

4. The detector of claim 1 wherein the re-emission sensor comprises a lens defining a contiguous multi-planar surface adjacent to the pathway and at least two focal points opposite the multi-planar surface.

5. The detector of claim 4 wherein the at least two focal points define a line that is substantially parallel to a line defined by the acquisition point and the privation point.

6. A particle detector comprising:
an interrogation chamber defining a pathway between an acquisition point and a privation point;
means for moving a carrier fluid through the pathway;
a photoexcitation source;
a re-emission sensor for detecting energy of a defined spectrum that is re-emitted by a particle that absorbs energy from at least one of the first beam and the second beam; and
a scanner disposed between the photoexcitation source and the re-emission sensor for scanning a beam from the photoexcitation source between the acquisition point and the privation point.

7. The particle detector of claim 6 wherein the scanner is controlled by the re-emission sensor at least when the beam is directed at the privation point.

8. The particle detector of claim 1 further comprising a trigger sensor for determining when a particle, carried by the carrier fluid, enters the chamber.

9. The particle detector of claim 8 further comprising a trigger energy source for emitting a trigger beam of a different spectrum than the first and second beam and wherein the trigger sensor detects energy scattered from the trigger beam by the particle.

10. The particle detector of claim 1 wherein the plurality of photoexcitation elements define a plurality of beams that impart energy to the particle as it moves along the pathway.

11. The particle detector of claim 10 wherein the plurality of beams impart energy to the particle in one of a continuous or periodic manner.

12. The particle detector of claim 1 wherein the plurality of photoexcitation elements are disposed along a line that substantially parallels a line defined by the acquisition point and the privation point.

13. The particle detector of claim 1 wherein the plurality of photoexcitation elements are disposed along at least two lines, each of which substantially parallels the line defined by the acquisition point and the privation point.

14. The particle detector of claim 1 wherein at least one of the plurality of photoexcitation elements comprises a first quantum well that emits energy of a first wavelength and a second quantum well that emits energy of a second wavelength different from the first.

15. The particle detector of claim 1 wherein the re-emission sensor comprises a collection lens having a convex surface adjacent to the pathway for directing at least a portion of a re-emission cone from both the acquisition point and the privation point to a collection point.

16. The particle detector of claim 15 wherein the re-emission sensor further comprises a spectrometer adjacent to the collection point.

17. The particle detector of claim 15 wherein the re-emission sensor further comprises an avalanche photodiode (APD) array and a spectrometer disposed between the APD array and the collection point.

18. A particle detector system comprising
a plurality of photoexcitation elements disposed within a planar source layer;
a plurality of sensor elements disposed along a planar sensor layer for sensing re-emitted energy from a particle; and
a capture layer disposed between the source layer and the sensor layer for binding with a target particle, at a location between a photoexcitation element and a sensor element, by one of electrostatic capture and molecular bonding.

19. The particle detector system of claim 18 disposed within a semiconductor based chipscale system, said system defining a first side and a second side each of which is no more than 10 cm long.

20. The particle detector system of claim 18 wherein the capture layer comprises at least one protein adapted for selective binding to the target particle.

21. The particle detector system of claim 18 wherein the capture layer is moveable relative to the source and sensor layer while the sensor elements sense re-emitted energy.

* * * * *